(12) United States Patent
Johnsen et al.

(10) Patent No.: US 8,917,268 B2
(45) Date of Patent: Dec. 23, 2014

(54) SYSTEMS AND METHODS FOR PERFORMING IMAGE BACKGROUND SELECTION

(75) Inventors: Robert John Johnsen, Waukesha, WI (US); Istvan Ubelhart, Budaors (HU); Ferenc Kovacs, Szeged (HU); Andras Kriston, Szeged (HU); Tamas Blaskovics, Szeged (HU)

(73) Assignee: General Electric Company, Schenectady, NY (US)

( * ) Notice: Subject to any disclaimer, the term of this patent is extended or adjusted under 35 U.S.C. 154(b) by 245 days.

(21) Appl. No.: 13/294,777

(22) Filed: Nov. 11, 2011

(65) Prior Publication Data

US 2013/0120443 A1 May 16, 2013

(51) Int. Cl.
| | |
|---|---|
| G09G 5/00 | (2006.01) |
| A61B 6/03 | (2006.01) |
| A61B 6/00 | (2006.01) |
| G01R 33/48 | (2006.01) |

(52) U.S. Cl.
CPC .............. *A61B 6/032* (2013.01); *A61B 6/037* (2013.01); *A61B 6/463* (2013.01); *A61B 6/5217* (2013.01); *A61B 6/5235* (2013.01); *A61B 6/4417* (2013.01); *G01R 33/481* (2013.01)
USPC ............... 345/418; 345/619; 600/442; 378/4; 382/131

(58) Field of Classification Search
CPC ............. G09G 5/14; G09G 2340/10; G09G 2340/125; G01S 7/52036; A61B 8/08; A61B 8/0875; A61B 6/032; G06T 2207/10081; G06T 7/0012; G06T 7/0083; G06F 19/321
USPC .......... 345/629, 418, 419, 619, 424; 382/131, 382/128; 600/442, 407, 427; 424/1.21; 435/7.1; 378/4

See application file for complete search history.

(56) References Cited

U.S. PATENT DOCUMENTS

| | | |
|---|---|---|
| 5,531,737 A | 7/1996 | Schade |
| 7,907,990 B2 | 3/2011 | Ferenczi et al. |
| 7,953,265 B2 | 5/2011 | Sirohey et al. |

(Continued)

FOREIGN PATENT DOCUMENTS

WO 2008/121367 A1 10/2008

OTHER PUBLICATIONS

Postert, et al., "Contrast Agent Specific Imaging Modes for the Ultrasonic Assessment of Parenchymal Cerebral Echo Contrast Enhancement", Journal of Cerebral Blood Flow and Metabolism, The International Society fore Cerebral Blood Flow and Metabolism, p. 1709-1716, 2000.*

(Continued)

*Primary Examiner* — Chante Harrison
(74) *Attorney, Agent, or Firm* — Lucas Divine; General Electric Company

(57) ABSTRACT

A method for automatically displaying an organ of interest includes accessing a series of medical images acquired from a first imaging modality, receiving an input that indicates an organ of interest, automatically detecting the organ of interest within at least one image in the series of medical images, automatically placing a visual indicator in the region of interest, and automatically propagating the visual indicator to at least one image that is acquired using a second different imaging modality. A medical imaging system and a non-transitory computer readable medium are also described herein.

15 Claims, 5 Drawing Sheets

(56) References Cited

U.S. PATENT DOCUMENTS

| | | | |
|---|---|---|---|
| 2004/0030246 A1* | 2/2004 | Townsend et al. | 600/427 |
| 2004/0106868 A1* | 6/2004 | Liew et al. | 600/442 |
| 2006/0004275 A1* | 1/2006 | Vija et al. | 600/407 |
| 2007/0217668 A1 | 9/2007 | Bornemann et al. | |
| 2008/0021301 A1* | 1/2008 | Gonzalez et al. | 600/407 |
| 2008/0107229 A1* | 5/2008 | Thomas et al. | 378/4 |
| 2008/0118132 A1 | 5/2008 | Ubelhart et al. | |
| 2010/0228727 A1* | 9/2010 | Hisanaga et al. | 707/723 |
| 2011/0007959 A1* | 1/2011 | Schulz et al. | 382/131 |
| 2011/0054295 A1* | 3/2011 | Masumoto et al. | 600/407 |
| 2011/0117572 A1* | 5/2011 | Kim et al. | 435/7.1 |
| 2011/0148861 A1* | 6/2011 | Boellaard | 345/419 |
| 2012/0170820 A1* | 7/2012 | Declerck et al. | 382/128 |
| 2012/0314925 A1* | 12/2012 | Peligrad | 382/131 |
| 2013/0034203 A1* | 2/2013 | Wang et al. | 378/41 |
| 2013/0129168 A1* | 5/2013 | Ross | 382/128 |
| 2013/0330274 A1* | 12/2013 | Berr et al. | 424/1.21 |

OTHER PUBLICATIONS

Search Report and Written Opinion from PCT Application No. PCT/US2012/060477 dated Mar. 6, 2013.

Bol G. H. et al., "Simultaneous multi-modality ROI delineation in clinical practice", Computer Methods and Programs in Biomedicine, Elsevier, Amsterdam, NL, vol. 96, No. 2, dated Nov. 1, 2009, pp. 133-140.

* cited by examiner

SYSTEMS AND METHODS FOR PERFORMING IMAGE BACKGROUND SELECTION

BACKGROUND OF THE INVENTION

The subject matter disclosed herein relates generally to imaging systems, and more particularly, to a method and system for performing image background selection.

In an oncology examination, a patient may go through a series of examinations, using for example, a computed tomography (CT) system, a positron emission tomography (PET) system, an ultrasound system, an x-ray system, a magnetic resonance (MR) system, a single photon emission computed tomography (SPECT) system, and/or other imaging systems. The series of examinations is performed to continuously monitor the patient's response to treatment. When evaluating a patient's response to treatment, the previous and follow-up examinations are often analyzed together. The results from the analysis of the follow-up examination may be saved together with results of the analysis of the previous examination(s). Accordingly, information on the progression of the disease throughout the whole series of examinations may be available to the clinician at any time from the same file and/or location.

However, when analyzing PET images to determine the progression of a disease, it may be difficult to identify the boundaries of an object of interest, such as for example, a lesion, when comparing the lesion for the same patient over time. As a result, a segmentation tool may be utilized to segment the lesion to enable the operator to determine the changes in the lesion over time.

At least one known segmentation tool separates the lesion from the normal background uptake in the patient and as such relies on sampling the normal uptake or background levels in the examination. In addition, when monitoring lesions over time, it is important to ensure consistent approaches are taken to lesion segmentation especially given that many factors may affect the background uptake levels.

Recent developments in therapy response monitoring, such as PERCIST (PET response criteria in solid tumors), rely on a more standardized approach to the process of classifying uptake at a lesion. The standardized approach may include, for example, specifications of uptake thresholds and techniques for background sampling that may include recommendations for locations and the sampling method. However, the standardized approach may be labor intensive and involve localizing the desired anatomy and then selecting and sizing the sampling tool. Moreover, additional steps may include fine tuning of the sampling region and pre to post therapy comparison and analysis of the results.

BRIEF DESCRIPTION OF THE INVENTION

In one embodiment, a method for automatically displaying an organ of interest is provided. The method includes accessing a series of medical images acquired from a first imaging modality, receiving an input that indicates an organ of interest, automatically detecting the organ of interest within at least one image in the series of the medical images, automatically placing a visual indicator in the region of interest, and automatically propagating the visual indicator to at least one image that is acquired using a second or different imaging modality.

In another embodiment, a medical imaging system is provided. The medical imaging system includes a detector array, and a computer coupled to the detector array. The computer is configured to access a series of computed tomography (CT) images, receive an input that indicates an organ of interest, automatically detect the organ of interest within at least one image in the series of CT images, automatically place a visual indicator in the region of interest, and automatically propagate the visual indicator to at least one image that is acquired using a second or different imaging modality.

In a further embodiment, a non-transitory computer readable medium is provided. The computer readable medium is programmed to instruct a computer to access a series of computed tomography (CT) images, receive an input that indicates an organ of interest, automatically detect the organ of interest within at least one image in the series of CT images, automatically place a visual indicator in the region of interest, and automatically propagate the visual indicator to at least one positron emission tomography (PET) image.

DETAILED DESCRIPTION OF THE INVENTION

Figure 1:
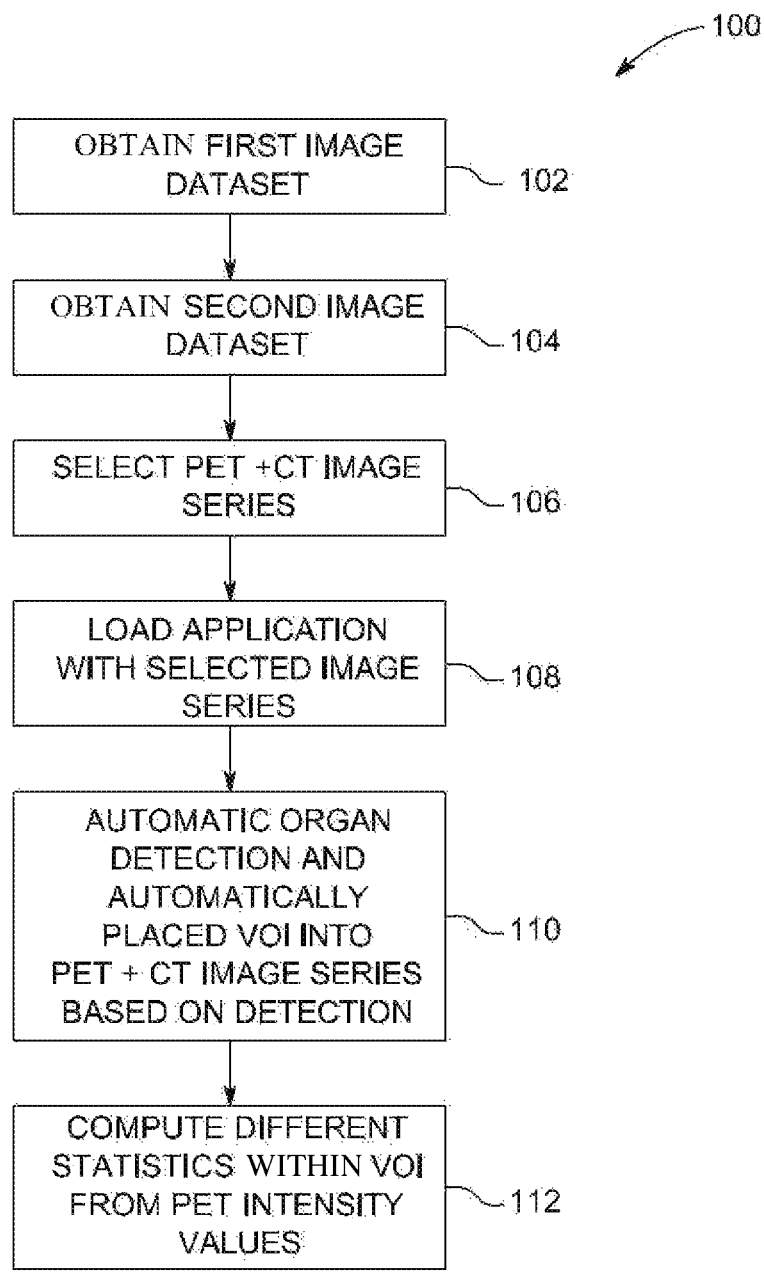
FIG. 1 is a flowchart of an exemplary method for automatically selecting and displaying a background region of an image in accordance with various embodiments.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

Described herein are various embodiments for automatically selecting, sampling, and computing one or more study appropriate background reference regions to improve a physician's ability to read and report a positron emission tomography (PET) examination. In various embodiments, the method includes utilizing a priori information of a clinical nature of the study and also the most appropriate background region for the study. In one exemplary embodiment, the method is described with respect to a PET study. The PET study may be implemented using images acquired from a PET/computed tomography (CT) imaging system.

Moreover, the study may be implemented using an imaging agent. The term "imaging agent," as used herein includes any and all radiopharmaceutical (RP) agents and contrast agents used in connection with diagnostic imaging and/or therapeutic procedures. The imaging agent may represent a perfusion agent. The imaging agent may be, among other things, an imaging agent adapted for use in magnetic resonance imaging (MRI) or functional MRI, an intravenous CT contrast agent, a radiopharmaceutical PET or single photon emission computed tomography (SPECT) tracer, an ultrasound contrast agent, an optical contrast agent, myocardial perfusion tracers, cerebral perfusion tracer and the like. By way of example only, the imaging agent may be Myoview™, Fluorodeoxyglucose (FDG), $^{18}$F-Flourobenzyl Triphenyl Phosphonium ($^{18}$F-FBnTP), $^{18}$F-Flouroacetate, $^{18}$F-labled myocardial perfusion tracers, Tc-ECD, Tc-HMPAO, N-13 ammonia, Envision N-13H3, Iodine-123 ligands, $^{99m}$-Technitium ligands, Xenon-133, Neuroreceptor ligands, etc.), 18F-fluoromisonidazole, $^{201}$Thallium, $^{99m}$Technetium sestamibi, and $^{82}$Rubidium among others.

In various embodiments, the imaging agent is selected based on the particular type of study desired. For example, the FDG agent may be utilized during a liver study. The various embodiments may be utilized by a variety of imaging modalities that include, for example, a CT imaging system and a PET imaging system and may also be extended to other combinations of PET imaging to provide study specific reference regions that may vary in terms of size, shape and/or location in the body.

In various embodiments, the most appropriate image data for localization of the desired PET reference region is selected. In the case of a hybrid PET/CT, for example, the CT images may be utilized. Calculations are then performed of the different features in the CT image. The calculations are then input to an algorithm that localizes, fine tunes, and/or validates the desired reference region. Once the calculations are validated, the reference region is projected onto a PET image and the statistics are automatically computed and displayed to the physician, e.g., an average uptake in the region, a standard deviation, etc.

FIG. 1 is a flowchart of an exemplary method 100 for automatically selecting and displaying a background region of an image. In the exemplary embodiment, the method 100 is embodied as an algorithm. The method 100 and/or the algorithm may be embodied as a set of instructions that are stored on a computer and implemented using, for example, a module 330, shown in FIG. 6, software, hardware, a combination thereof, or a tangible non-transitory computer readable medium.

Referring again to FIG. 1, the method 100 includes obtaining at 102 a first image dataset of a patient. By way of example only, the first image dataset may be a baseline image dataset that provides a reference for future image datasets. The first image dataset may be acquired by retrieving the image dataset from a database or, alternatively, receiving the first image dataset from an imaging system. The first image dataset may include, for example, a series of medical images taken along an examination axis. In the exemplary embodiment, the series of medical images include a series of cross-sectional images (or slices) of a volume of interest (VOI) of the patient. The cross-sectional images may have a predetermined thickness (e.g., 1.25 mm, 5 mm) in which each image includes a cross-section of one or more anatomical structures of the patient. As a specific example, the first image dataset may include a series of CT images of the patient's liver. The first image dataset may also include three-dimensional (3D) medical images. The first image dataset may also include a series of PET images. The first image dataset may include a series of images acquired from any two imaging modalities described herein.

At 104, a second different image dataset of the patient may be obtained. The second image dataset may include, for example, a second series of medical images. The second image dataset may be medical images acquired from a later imaging session. The second image dataset may be acquired by retrieving the image dataset from a database or, alternatively; receiving the second image dataset from an imaging system. The second image dataset may also include a series of PET images. Optionally, the second image dataset may include a series of images acquired from any of the imaging modalities described herein. It should be realized that the first and second image datasets may also be a series of fused images. For example, the first image dataset may include a plurality of CT images that are fused or registered with a plurality of PET images. Similarly, the second dataset may include a plurality of CT images that are fused or registered with a plurality of PET images.

At 106, an operator selects a series of images. In various embodiments, the operator may select a series of PET images acquired at any time point. Optionally, the operator may select a fused set of CT/PET images, etc. In the exemplary embodiment, the operator selects the first series of CT images. At 108, the selected series of images are automatically accessed or obtained by the algorithm.

At 110, automatic organ detection is performed using the automatically accessed series of images. More specifically, the method 100 enables fully automatic detection of a selected organ, such as for example, the liver. Moreover, the method automatically places a visual indication on a reference region in the image that indicates a region of interest (ROI) and/or VOI that includes the liver. While various embodiments are described with respect to automatically detecting a liver, it should be realized that other objects and/or organs of interest may be detected. For example, such objects may include metastatic lesions in the bone or the brain. If the liver is diseased, a reference region in the blood pool from the descending aorta may be detected. The organ to be detected may be based on the specific tracer being utilized during the examination. In the exemplary embodiment, the tracer is FDG and the liver is automatically detected. The series of CT images may be registered with a series of PET images. Accordingly, a display device may enable an operator to view one or more CT images, one or more PET images, and/or one or more registered CT/PET images.

Figure 2:
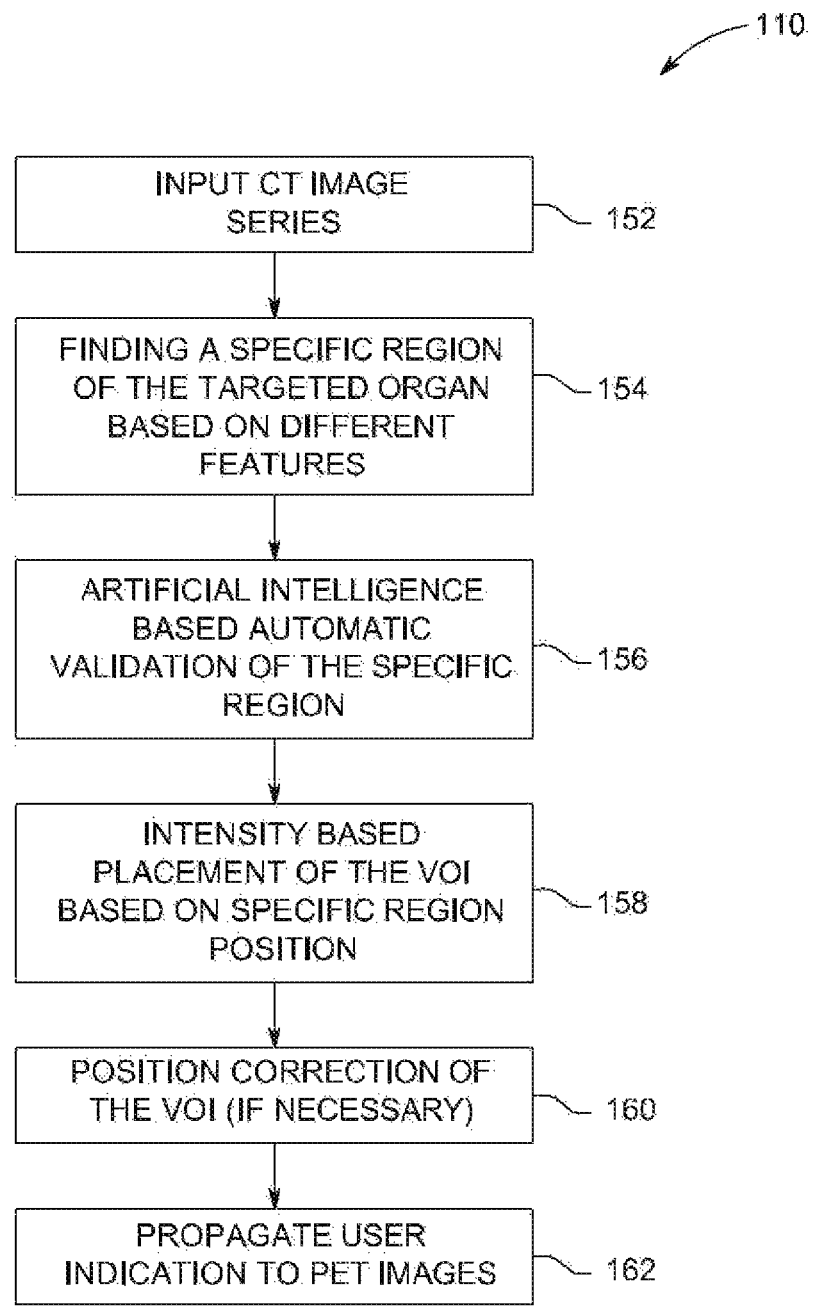
FIG. 2 is another flowchart of a portion of the method shown in FIG. 1 in accordance with various embodiments.

FIG. 2 is a flowchart illustrating an exemplary method of implementing step 110 shown in FIG. 1. At 152 the series of CT images selected at 106 are input to or obtained by the algorithm. It should be realized that the series of CT images show some tracer uptake in the reference region, e.g. the liver. In the exemplary embodiment, the series of CT images is initially utilized because CT images provide an enhanced anatomical view of the reference region to the operator.

At 154, a specific region of interest is identified. The specific region of interest may be, for example, a region of the targeted organ, e.g. the liver. In the exemplary embodiment, the targeted organ is designated by the operator prior to implementing step 154. In various embodiments, the targeted organ, or a specific region of the targeted organ, is automatically identified based on a priori information of the targeted organ. For example, assuming that the targeted organ is the liver, the algorithm utilizes a priori information of the liver to identify the region of interest within at least one CT image in the series of CT images.

Such a priori information may include, for example, an expected liver intensity. More specifically, the a priori information may include information of various liver studies that have been previously performed. Based on the previous studies, the a priori information may include pixel intensity values that represent known livers. Thus, assuming that the algorithm has information of pixel intensity values that more than likely represent pixels of the liver, the algorithm may utilize this information to locate the liver in at least one image in the series of CT images. In the exemplary embodiment, each CT image in the series of CT images is thresholded, using the a priori pixel intensity values of a liver, to identify whether that particular slice includes a portion of the liver. More specifically, the algorithm may access a predetermined range of pixel densities that are associated with the liver. The algorithm then searches the series of CT images, on a slice by slice basis, to identify all pixels having an intensity that falls within the predetermined range. In other embodiments, the a priori information may include soft tissue intensity values of areas known to surround the liver. In the exemplary embodiment, at 154, each slice or image in the series of CT images is classified as either having a portion of the liver or not have a portion of the liver to generate a list of slices that potentially include a portion of the liver.

Figure 3:
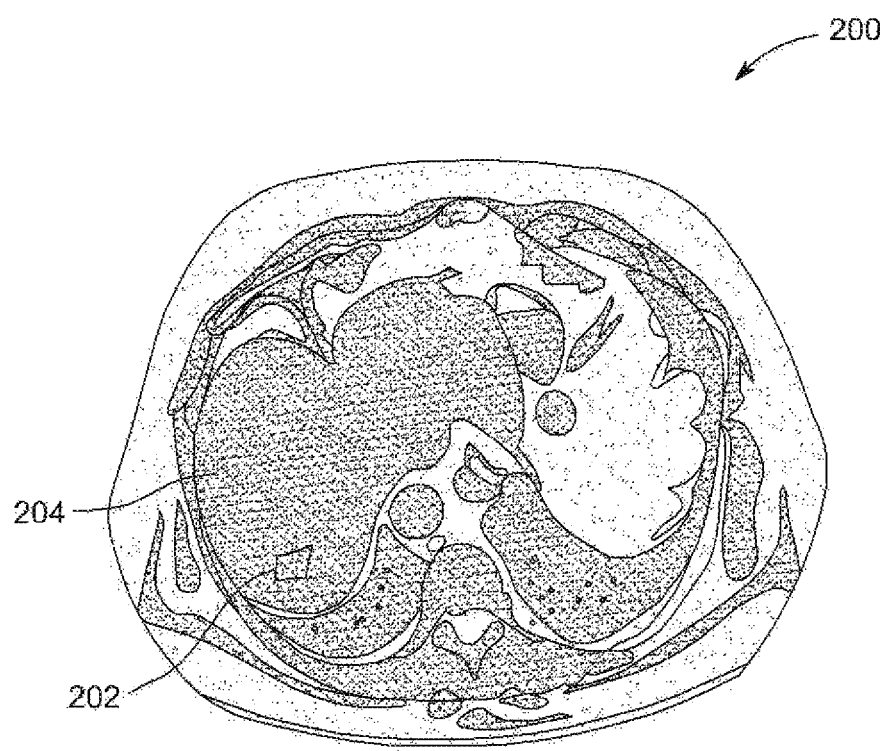
FIG. 3 is an exemplary image that may be generated in accordance with various embodiments.

At 156, the algorithm accesses the list of slices that potentially include a portion of the liver generated at 154. The algorithm then automatically selects a single slice from the list of slices that best represents the liver. For example, FIG. 3 illustrates an exemplary CT image slice 200 that may be automatically selected from the list of CT slices generated at 154. In various embodiments, the term "best represents" as used herein means the slice that includes a representation of the liver that meets the most criteria from a list of criteria. For example, the list of criteria may include, for example, the slice that shows the largest area of the liver or the best view of the liver. It should be realized that the a priori information may also include the type of examination being performed. As a result, the system receives inputs identifying the types of images that the operator may need to perform a specific type of diagnosis. Accordingly, the algorithm has a priori information on the type, view, etc., of the liver that the operator is requesting. Thus, the algorithm may utilize this a priori information to identify a single slice, e.g. the slice 200 that shows the liver from a view that best enables the operator to perform the diagnosis.

The algorithm may utilize artificial intelligence (AI) sub-algorithms to identify the slice that includes the liver. More specifically, the algorithm may be trained using a large set of known livers to generate a liver training dataset. It should be realized that although the exemplary embodiment is described with respect to identifying a liver, the training dataset may be utilized to train the algorithm to identify various other organs or structures. In operation, the training dataset may include information of the shape of an exemplary liver that is based on a shape of a plurality of known livers. Thus, the outline or shape of the suspected liver region in the CT image may be calculated and then compared to known livers to determine whether the region suspected to define the liver does in fact define the liver. In another embodiment, the size of the suspected liver region may be compared to known livers having a known size. Moreover, the sizes may be based on the age of a patient. Thus, the training dataset may include a priori patient information that includes not only the age of the patient, but also, the size of a normal liver representative of patients of that particular age.

The training datasets may also be obtained using automatic information gathering techniques. For example, the training dataset may be formed by compiling statistics of a plurality of patient's ages, size of the liver for a patient of a certain age, etc. Thus, the training dataset includes information that describes various liver parameters based on the age of the patient, size of the liver, etc., from known good livers. In other embodiments, the liver may be identified by comparing objects within the CT image to other objects within the CT image. For example, it is known that the liver is the largest organ in the chest cavity. Thus, the algorithm may determine a shape and/or size of various organs or objects within the chest cavity and identify the largest object as the liver. Accordingly, at 156, the algorithm selects a single CT slice or image from the list of CT images that provides the best visual representation of the liver based on the examination procedure being performed. Additionally, the algorithm places a visual indicator 202 that represents the initial ROI or VOI within the image of the liver. In various embodiments, the visual indicator 202 may have a cubed spherical shape that may have any user defined size or shape.

Referring again to FIG. 2, at 158, the initial ROI defined in the single CT slice at 156 is automatically transferred to the remaining CT images in the series of CT images. Referring again to FIG. 3, the image 200 is shown as including an initial ROI 202 that is placed within a liver 204. In the exemplary embodiment, the coordinates of the ROI of the liver 204 in the single CT slice are initially calculated. A visual indication representing the ROI is then automatically transferred to the remaining CT images slices and positioned at the same coordinates of the liver 204 indicated in the single CT slice. Thus, the liver 204 in each slice, in the series of CT slices, includes a visual indicator 202 representing the initial ROI, e.g. the liver 204. Accordingly, at 158, the visual indicator 202 outlining the initial VOI or ROI 204 is automatically placed on the CT image slice 200.

At 160, the visual indication 202, that is automatically located at a predetermined position within the liver 204 at 158, may be automatically adjusted by the algorithm. In operation, the location of the visual indicator 202 may be adjusted based on the pixel intensities of the initial ROI defined within the visual indicator 202. More specifically, a filter may be utilized to filter regions in the liver 204 having stronger intensity values, to filter tumourous regions, to filter regions near the edge of the liver 204, to filter regions near the bone, and/or to move the initial ROI position inside the liver 204 to a final position based upon the results of the filtering.

In the exemplary embodiment, the visual indicator 202 is placed in the lower lobe of the liver 204 as shown in FIG. 3. In operation, the algorithm locates the lower lobe of the liver 204 using various techniques. The algorithm may select the region of the liver 204 to place the visual indication 202 based upon the intensity values within the liver 204. For example, a predetermined pixel value may be entered into the algorithm by the user. The predetermined pixel values may be a single value or a range of pixel intensity values. The pixel intensity value is based on a priori information of the pixel intensity values of known good livers. The location of the visual indication 202 may then be determined by analyzing all the pixel intensity values of the region of the liver 204. The final position of the visual indication 202 on the image 202 may then be automatically determined by, for example, weighting the pixel intensity values to determine a weighted average of all the pixels forming the liver 204 in the image 202. The visual indication 202 may then be automatically positioned at the point wherein the pixels encompassed by the visual indication 202 are within the weighted average and/or are within the predetermined range of pixel values. In operation, the pixel intensity values of the liver 204 enable the algorithm to automatically identify a soft tissue region of the liver 204 and then later to refine the position of the initial location of the visual indicator 202 within the liver 204. Accordingly, at 158, the visual indication 202 is automatically placed on the image 200 at an initial position in the region of the liver 204 based on the coordinates of the liver 204. Once the visual indication 202 is roughly placed on the image 200, the location of the visual indication 202 may be refined based on the pixel intensity values of the liver 204. Accordingly, at 160, the image 200 includes the visual indication 202 placed at the final location on the liver 204.

Figure 4:
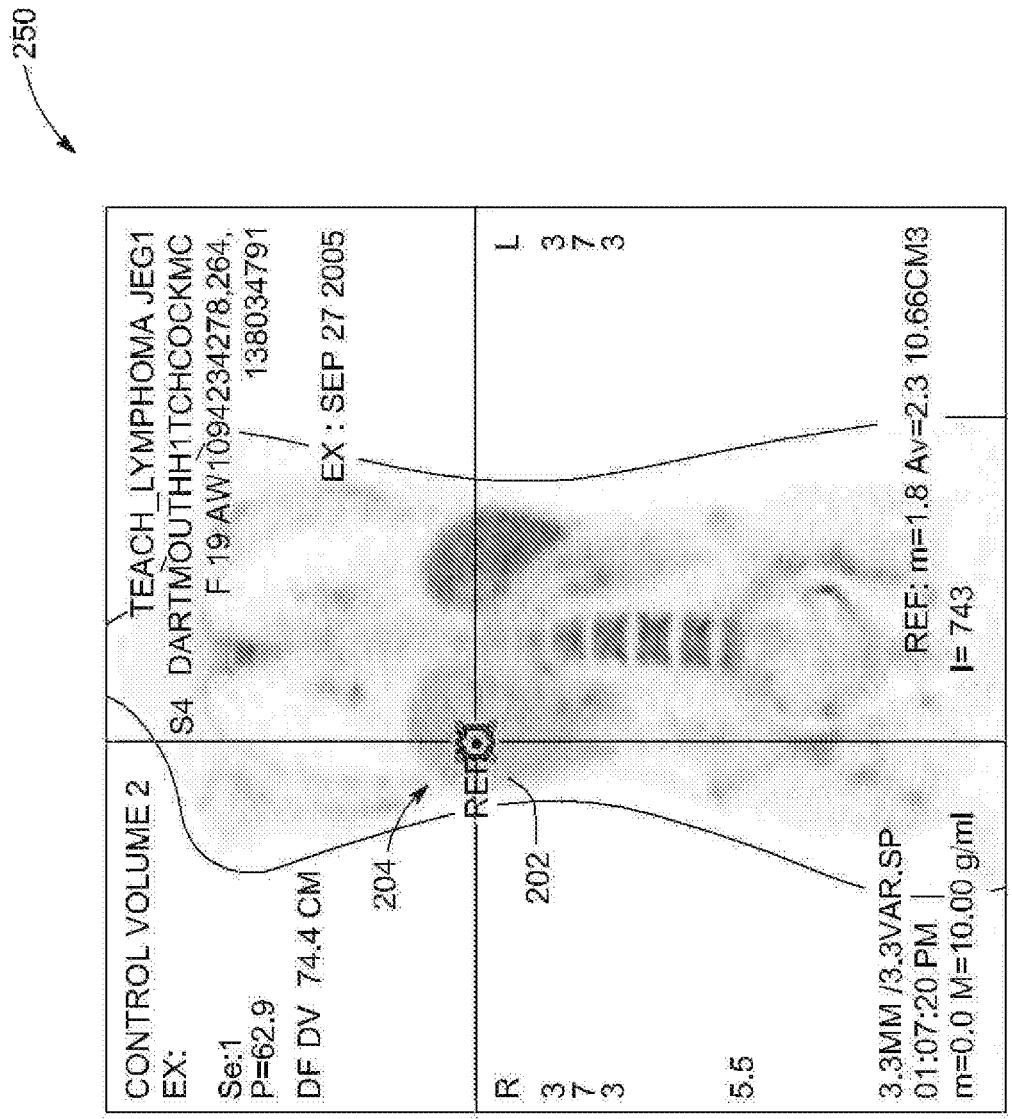
FIG. 4 is another exemplary image that may be generated in accordance with various embodiments.

Referring again to FIG. 2, at 162, the visual indication 202 is propagated from the CT image 200 to at least one PET image. For example, the visual indication 202 may be propagated to an exemplary PET image 250 as shown in FIG. 4. In the exemplary embodiment, the CT image 200 forms a portion of the series of CT images. Moreover, as described above, the series of CT images are registered with the series of PET images using any suitable image registration technique. Thus, at 162, the visual indication 202 is propagated from the CT image 200 to each of the CT images in the series of CT images. Moreover, because the series of CT images are registered with the series of PET images, the visual indication 202 is propagated to each PET image in the series of PET images.

After the visual indication 202, representing the VOI, has been propagated from the CT images to the PET images, the visual indication 202 may then again be adjusted. In some embodiments, the visual indication 202, once shown in the PET images, may be blocked or partially obscured by other features shown on the PET images. For example, at least some of the PET images may include a liver having a diseased portion which may block or obscure a portion of the visual indication 202. In this case, the algorithm may be programmed to prompt the operator to reposition the visual indication 202 to a different location of the liver 204 that is, for example, not diseased. Accordingly, in various embodiments, the visual indication 202 on the PET image 250 may be manually or automatically repositioned to a second location based on the pixel intensity values within the PET image. To determine the pixel intensity values within the PET images, at least one of the PET images may be segmented to show only the liver 204, or any other selected ROI. The overall average of the pixel intensity values within the ROI may then be calculated to determine the final location of the visual indication 202. Optionally, the CT image 200 may be segmented. Because the CT images are registered with the PET images, the segmented CT image may be utilized to segment the PET images.

Referring again to FIG. 2, at 112 various statistics of the ROI encompassed by the visual indication 202 may be automatically calculated. The statistics may include, for example, an average pixel intensity value within the visual indication 202, a volume encompassed by the visual indication 202, a maximum pixel intensity value within the visual indication 202, and/or a standard deviation of pixel values within the visual indication 202. In various embodiments, the above described statistics may also be automatically generated for the entire liver region. In one embodiment, if the statistics within the visual indication 202 are different than the related statistics outside the visual indication 202, the operator may manually move the visual indication 202. Optionally, the algorithm may automatically reposition the visual indication 202 based on the computed statistics.

In operation, at least some of the various statistics may be visually displayed to the operator. For example, and referring again to FIG. 4, the term "Ref" denotes the visual indication 202 which may have a square or spherical shape as described above. The letter "m" denotes a value of the pixel having the lowest intensity value. In the exemplary embodiment, m=1.8. Therefore, in the exemplary embodiment, the lowest pixel intensity value is 1.8. Moreover, the term "Av" denotes the average pixel intensity value. Thus, in the exemplary embodiment, the average intensity value for all the pixels is 2.3. Additionally, the volume of the region encompassed by the visual indication is, in one embodiment, 10.66 cubic centimeters. In various embodiments, the PET image 250 may be scaled in units of gram per milliliter (g/ml) of uptake to enable the operator to compare the g/ml in the region encompassed by the visual indication 202 with the region outside the visual indication 202.

Various embodiments described herein provide a method and/or algorithm for automatically selecting, sampling and computing one or more study appropriate background reference regions to facilitate the physician's ability to read and/or report a PET exam. The method utilizes a priori information that includes the clinical nature of the study and also the most appropriate background region for the study. In various embodiments the method is described with respect to a PET/CT examination being performed using the radionuclide FDG. However, it should be realized that the methods described herein may also be performed using various other studies. For example, an MRI image may be utilized to place the visual indication 202 on the PET image 250, etc. Accordingly, in various embodiments, the methods described herein may be utilized with other combinations of PET imaging to provide study specific reference regions that vary in terms of size, shape or location in the body.

In various embodiments, the method includes selecting the most appropriate image data for localization of the desired PET reference region. In the case of a hybrid PET/CT, a CT image is utilized. Calculations are then performed of the different features along the CT image and input to an algorithm that localizes, fine tunes, and validates the desired reference region, e.g., the location of the visual indication 202. Once validated, the reference region is projected onto the PET images and the statistics are automatically computed and displayed to the physician (e.g. average uptake in the region, standard deviation etc.)

Figure 5:
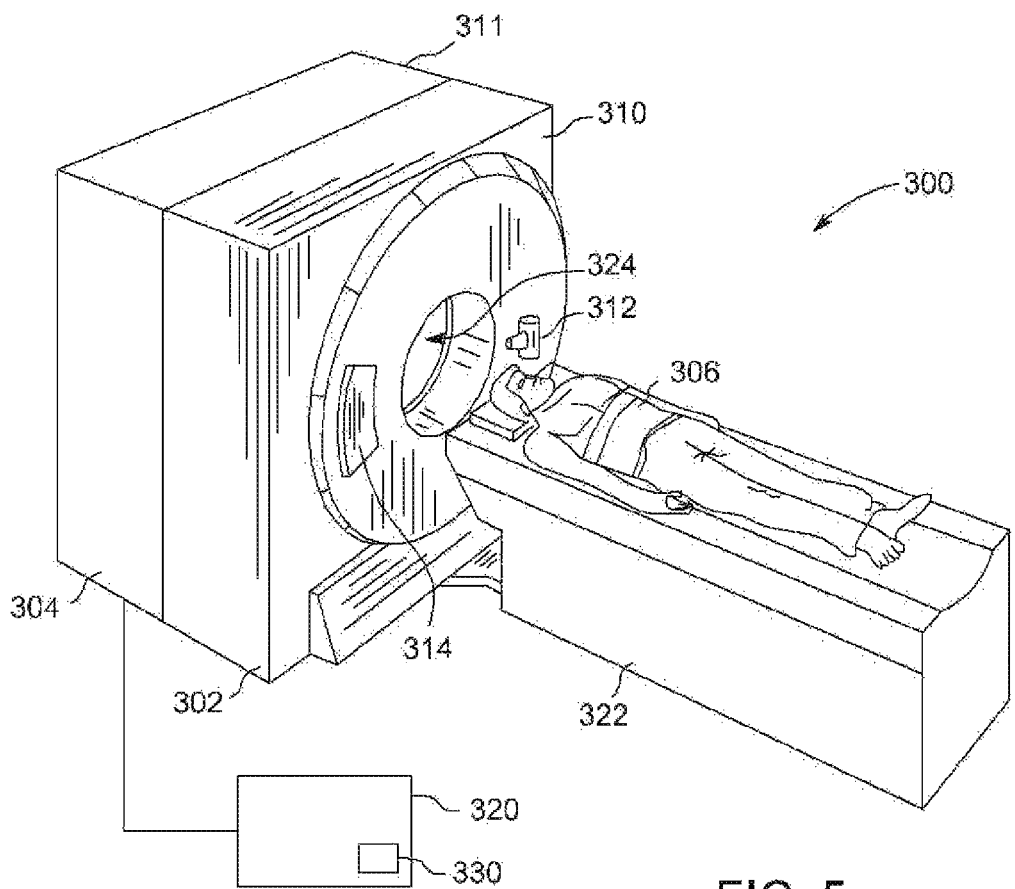
FIG. 5 is a pictorial view of an exemplary multi-modality imaging system formed in accordance with various embodiments.
Figure 6:
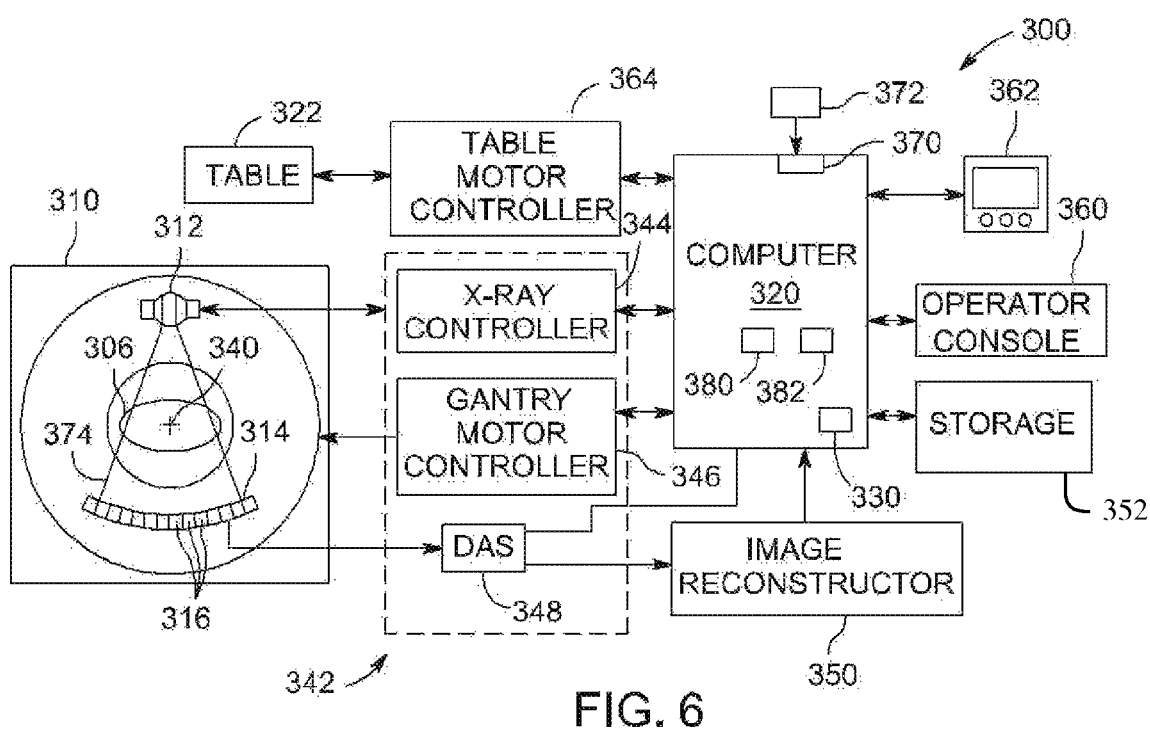
FIG. 6 is a block schematic diagram of the system illustrated in FIG. 5.

FIG. 5 is a pictorial view of an exemplary imaging system 300 that is formed in accordance with various embodiments. FIG. 6 is a block schematic diagram of a portion of the multi-modality imaging system 300 shown in FIG. 5. Although various embodiments are described in the context of an exemplary dual modality imaging system that includes a CT imaging system and a PET imaging system, it should be understood that other imaging systems capable of performing the functions described herein are contemplated as being used.

The multi-modality imaging system 300 is illustrated, and includes a CT imaging system 302 and a PET imaging system 304. The imaging system 300 allows for multiple scans in different modalities to facilitate an increased diagnostic capability over single modality systems. In one embodiment, the exemplary multi-modality imaging system 300 is a CT/PET imaging system 300. Optionally, modalities other than CT and PET are employed with the imaging system 300. For example, the imaging system 300 may be a standalone CT imaging system, a standalone PET imaging system, a magnetic resonance imaging (MRI) system, an ultrasound imaging system, an x-ray imaging system, and/or a single photon emission computed tomography (SPECT) imaging system, interventional C-Arm tomography, CT systems for a dedicated purpose such as extremity or breast scanning, and combinations thereof, among others.

The CT imaging system 302 includes a CT gantry 310 and a PET gantry 311. The gantry 310 has an x-ray source 312 that projects a beam of x-rays toward a detector array 314 on the opposite side of the gantry 310. The detector array 314 includes a plurality of detector elements 316 that are arranged in rows and channels that together sense the projected x-rays that pass through an object, such as the subject 306. The imaging system 300 also includes a computer 320 that receives the projection data from the detector array 314 and processes the projection data to reconstruct an image of the subject 306. In operation, operator supplied commands and parameters are used by the computer 320 to provide control signals and information to reposition a motorized table 322. More specifically, the motorized table 322 is utilized to move the subject 306 into and out of the gantry 310. Particularly, the table 322 moves at least a portion of the subject 306 through a gantry opening 324 that extends through the gantry 310.

The imaging system 300 also includes a module 330 that is configured to implement various methods and algorithms described herein. The module 330 may be implemented as a piece of hardware that is installed in the computer 320. Optionally, the module 330 may be implemented as a set of instructions that are installed on the computer 320. The set of instructions may be stand alone programs, may be incorporated as subroutines in an operating system installed on the computer 320, may be functions in an installed software package on the computer 320, and the like. It should be understood that the various embodiments are not limited to the arrangements and instrumentality shown in the drawings. Accordingly, in the exemplary embodiment, the module 330 includes a set of instructions, such as for example the algorithm, that enables the computer 330 to perform the various methods described herein.

As discussed above, the detector 314 includes a plurality of detector elements 316. Each detector element 316 produces an electrical signal, or output, that represents the intensity of an impinging x-ray beam and hence allows estimation of the attenuation of the beam as it passes through the subject 306. During a scan to acquire the x-ray projection data, the gantry 310 and the components mounted thereon rotate about a center of rotation 340. FIG. 6 shows only a single row of detector elements 316 (i.e., a detector row). However, the multislice detector array 314 includes a plurality of parallel detector rows of detector elements 316 such that projection data corresponding to a plurality of slices can be acquired simultaneously during a scan.

Rotation of the gantry 310 and the operation of the x-ray source 312 are governed by a control mechanism 342. The control mechanism 342 includes an x-ray controller 344 that provides power and timing signals to the x-ray source 312 and a gantry motor controller 346 that controls the rotational speed and position of the gantry 310. A data acquisition system (DAS) 348 in the control mechanism 342 samples analog data from detector elements 316 and converts the data to digital signals for subsequent processing. For example, the subsequent processing may include utilizing the module 330 to implement the various methods described herein. An image reconstructor 350 receives the sampled and digitized x-ray data from the DAS 348 and performs high-speed image reconstruction. The reconstructed images are input to the computer 320 that stores the image in a storage device 352. In the exemplary embodiment, the reconstructed images may include a series of CT images 380 and a series of PET images 382. Optionally, the computer 320 may receive the sampled and digitized x-ray data from the DAS 348 and perform various methods described herein using the module 330. The computer 320 also receives commands and scanning parameters from an operator via a console 360 that has a keyboard. An associated visual display unit 362 allows the operator to observe the reconstructed image and other data from computer.

The operator supplied commands and parameters are used by the computer 320 to provide control signals and information to the DAS 348, the x-ray controller 344 and the gantry motor controller 346. In addition, the computer 320 operates a table motor controller 364 that controls the motorized table 322 to position the subject 306 in the gantry 310. Particularly, the table 322 moves at least a portion of the subject 306 through the gantry opening 324 as shown in FIG. 5.

Referring again to FIG. 6, in one embodiment, the computer 320 includes a device 370, for example, a non-transitory computer readable medium such as, for example, a floppy disk drive, CD-ROM drive, a DVD drive, a magnetic optical disk (MOD) device, or any other digital device including a network connecting device such as an Ethernet device for reading instructions and/or data from a computer-readable medium 372, such as a floppy disk, a CD-ROM, a DVD or an other digital source such as a network or the Internet, as well as yet to be developed digital means. In another embodiment, the computer 320 executes instructions stored in firmware (not shown). The computer 320 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the x-ray source 312 and the detector array 314 are rotated with the gantry 310 within the imaging plane and around the subject 306 to be imaged such that the angle at which an x-ray beam 374 intersects the subject 306 constantly changes. A group of x-ray attenuation measurements, i.e., projection data, from the detector array 314 at one gantry angle is referred to as a "view". A "scan" of the subject 306 comprises a set of views made at different gantry angles, or view angles, during one revolution of the x-ray source 312 and the detector 314. In a CT scan, the projection data is processed to reconstruct an image that corresponds to a two dimensional slice taken through the subject 306.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software, which may be a non-transitory computer readable medium. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A medical imaging system comprising:
    a detector array; and
    a computer coupled to the detector array, the computer configured to
        access a first series of images acquired using a computed tomography (CT) imaging modality;
        receive predetermined pixel intensity values that indicate an organ of interest;
        threshold each image slice in the first series of images using the predetermined pixel intensity values to identify pixels in each image slice that indicate the organ of interest;
        automatically select a single image slice from the first series of images that best represents the organ of interest;
        automatically place a first visual indicator designating a region of interest (ROI) in the single image slice that best represents the organ of interest;
        automatically transfer the first visual indicator representing the ROI to the remaining image slices in the first series of images;
        automatically analyze the ROI designated by the first visual indicator within the first series of images based on first ROI pixel intensity values;
        automatically propagate a second visual indicator, designating the ROI, onto at least one second image from a second series of images using a second imaging modality based on a final position of the ROI in the first series of images;
        automatically analyze the ROI designated by the second visual indicator within the second image based on second ROI pixel intensity values; and
        automatically reposition the second visual indicator based on at least the first ROI pixel intensity values and the second ROI pixel intensity values.

2. The medical imaging system of claim 1, wherein the computer is further configured to utilize a plurality of predetermined criteria to automatically identify the region of interest in the CT image.

3. The medical imaging system of claim 1, wherein the organ of interest is a liver.

4. The medical imaging system of claim 1, wherein the computer is further configured to:
    register the CT images with a series of PET images.

5. The medical imaging system of claim 1, wherein the computer is further configured to:
    automatically compute statistics for an area within the visual indication and another area outside the visual indicator.

6. The medical imaging system of claim 1, wherein the computer is further configured to prompt an operator to reposition the visual indicator based on a plurality of determined statistics.

7. A non-transitory computer readable medium being programmed to instruct a computer to:
- access a series of computed tomography (CT) images;
- receive predetermined pixel intensity values that indicate an organ of interest;
- threshold each image slice in the series of CT images using the predetermined pixel intensity values to identify pixels in each image slice that indicate the organ of interest;
- automatically select a single image slice that best represents the organ of interest;
- automatically place a first visual indicator designating a region of interest (ROI) in the single image slice that best represents the organ of interest;
- automatically transfer the first visual indicator representing the ROI to the remaining image slices in the series of CT images;
- automatically analyze the ROI designated by the first visual indicator within the series of CT images based on first ROI pixel intensity values;
- automatically propagate a second visual indicator, designating the ROI, onto at least one positron emission tomography (PET) image;
- automatically analyzing the ROI designated by the second visual indicator within the PET image based on second ROI pixel intensity values; and
- automatically reposition the second visual indicator based on at least the first ROI pixel intensity values and the second ROI pixel intensity values.

8. The non-transitory computer readable medium of claim 7, wherein the computer utilizes a plurality of predetermined criteria to automatically identify the region of interest in the CT image.

9. The non-transitory computer readable medium of claim 7, wherein the organ of interest is the liver.

10. A method for automatically displaying an organ of interest, said method comprising:
- accessing a first series of images acquired using a first imaging modality and a second series of images acquired using a second imaging modality;
- receiving predetermined pixel intensity values that indicate an organ of interest;
- thresholding each image slice in the first series of images using the predetermined pixel intensity values to identify pixels in each image slice that indicate the organ of interest;
- automatically select a single image slice that best represents the organ of interest;
- placing a first visual indicator designating a region of interest (ROI) in the single image slice that best represents the organ of interest;
- transferring the first visual indicator representing the ROI to the remaining image slices in the first series of images;
- automatically analyzing the region of interest designated by the first visual indicator within the first series of images based on first ROI pixel intensity values;
- automatically propagating a second visual indicator, designating the ROI, onto at least one second image from a second series of images based on a final position of the ROI in the first series of images; and
- automatically analyzing the region of interest designated by the second visual indicator within the second image based on second ROI pixel intensity values;
- automatically repositioning the second visual indicator based on at least the first ROI intensity values and the second ROI pixel intensity values.

11. The method of claim 10, wherein the first imaging modality comprises a computed tomography (CT) imaging system or a magnetic resonance imaging (MRI) system and the second imaging modality comprises a positron emission tomography (PET) system.

12. The method of claim 10, wherein the organ of interest is a liver.

13. The method of claim 10, further comprising:
- registering the series of images acquired from the first imaging modality with a series of images acquired from the second imaging modality.

14. The method of claim 10, further comprising prompting an operator to reposition the visual indicator based on a plurality of determined statistics.

15. The method of claim 10, wherein the repositioning of the second visual indicator is further based on at least one of a weighted average of the pixel intensity values, a standard deviation from the average pixel intensity value, a maximum pixel intensity value, or a predetermined range of pixel value.

* * * * *